US012344827B2

(12) United States Patent
Serpooshan et al.

(10) Patent No.: US 12,344,827 B2
(45) Date of Patent: Jul. 1, 2025

(54) AUTOMATIZED, PROGRAMMABLE, HIGH-THROUGHPUT TISSUE CULTURE AND ANALYSIS SYSTEMS AND METHODS

(71) Applicant: Emory University, Atlanta, GA (US)

(72) Inventors: Vahid Serpooshan, Atlanta, GA (US); Ayda Melika, Atlanta, GA (US); Amir Pourmorteza, Atlanta, GA (US)

(73) Assignee: Emory University, Atlanta, GA (US)

( * ) Notice: Subject to any disclaimer, the term of this patent is extended or adjusted under 35 U.S.C. 154(b) by 1069 days.

(21) Appl. No.: 17/260,946

(22) PCT Filed: Jul. 17, 2019

(86) PCT No.: PCT/US2019/042295
§ 371 (c)(1),
(2) Date: Jan. 15, 2021

(87) PCT Pub. No.: WO2020/018725
PCT Pub. Date: Jan. 23, 2020

(65) Prior Publication Data
US 2021/0324315 A1     Oct. 21, 2021

Related U.S. Application Data

(60) Provisional application No. 62/699,478, filed on Jul. 17, 2018.

(51) Int. Cl.
*C12M 1/00* (2006.01)
*C12M 1/36* (2006.01)
*C12M 3/06* (2006.01)

(52) U.S. Cl.
CPC ............ *C12M 23/16* (2013.01); *C12M 23/38* (2013.01); *C12M 29/00* (2013.01); *C12M 31/02* (2013.01); *C12M 41/48* (2013.01)

(58) Field of Classification Search
CPC ......... B01L 2300/041; B01L 2300/046; B01L 2300/0654; B01L 2300/0816;
(Continued)

(56) References Cited

U.S. PATENT DOCUMENTS 6,673,595 B2    1/2004   Barbera-Guillem
8,318,479 B2    11/2012  Domansky et al.
(Continued)

FOREIGN PATENT DOCUMENTS

EP       1 461 592 B1       4/2019
WO    WO 2005/010162 A2    2/2005
(Continued)

OTHER PUBLICATIONS

Cooksey et al. "Evaluating Measurement Quality of Microfluidic Cell-based Assays." NIST. Feb. 2017 [online], [retrieved on Jan. 23, 2025]. Retrieved from the Internet <URL: https://www.nist.gov/system/files/documents/mml/bbd/cell_systems/8c_bio.pdf>.
(Continued)

*Primary Examiner* — Lydia Edwards
(74) *Attorney, Agent, or Firm* — Emory Patent Group

(57) ABSTRACT

In some embodiments, the systems and methods of the disclosure can provide high-throughput, programmable, and fully automatized tissue and/or cell culture and analysis platforms. In some embodiments, a culture analysis system may include a culture device that includes a cover configured to be secured to a main body, which may include one or more chambers. The cover may include one or more regions that overlaps with the one or more chambers of the main body when the cover is secured to a main body so that each region corresponds to a chamber of the main body. The cover may also include a fluidic pathway disposed in each region and configured be in fluidic communication with a corresponding chamber. Each fluidic pathway may include a
(Continued)

fluid inlet and a fluid outlet disposed in each region. The cover may also include an optical pathway disposed in each region for the corresponding chamber.

20 Claims, 10 Drawing Sheets

(58) Field of Classification Search
CPC ...... B01L 2300/0861; B01L 3/502715; C12M 23/16; C12M 23/38; C12M 29/00; C12M 31/02; C12M 41/48; G01N 33/48
See application file for complete search history.

(56) References Cited

U.S. PATENT DOCUMENTS

| | | |
|---|---|---|
| 9,550,970 B2 | 1/2017 | Hammons et al. |
| 2006/0050376 A1 | 3/2006 | Houston et al. |
| 2006/0199260 A1* | 9/2006 | Zhang .................... C12M 23/24 435/293.1 |
| 2010/0112690 A1* | 5/2010 | Eddington .............. C12M 23/12 435/297.5 |
| 2013/0143230 A1 | 6/2013 | Tolias et al. |
| 2018/0282682 A1 | 10/2018 | Pebay et al. |

FOREIGN PATENT DOCUMENTS

| | | | |
|---|---|---|---|
| WO | WO 2007/056512 A2 | 5/2007 | |
| WO | WO 2008/118500 A1 | 10/2008 | |
| WO | WO 2015/023658 A2 | 2/2015 | |
| WO | WO-2019014151 A1 * | 1/2019 | .......... B01L 3/50853 |
| WO | WO 2019/043130 A1 | 3/2019 | |

OTHER PUBLICATIONS

Domansky et al. "Perfused Multiwell Plate for 3D Liver Tissue Engineering." Lab Chip. 2010; 10(1):51-58.
Huang et al. "development of pneumatically driven active cover lid for multi-well microplates for use in perfusion three-dimensional cell culture." Scientific Reports. 2015; 5:18352.
Huttunen et al. "An automated continuous monitoring system: a useful tool for monitoring neuronal differentiation of human embryonic stem cells." Stem Cell Studies. 2011; 1 (e10):71-77.
Jain et al. "The Complete Automation of Cell Culture: Improvements for High-Throughput and High-Contrast Screening." Journal of Biomolecular Screening. 2011; 16:935-939.
International Search Report and Written Opinion for PCT Application No. PCT/US2019/042295 dated Nov. 8, 2019.

* cited by examiner

AUTOMATIZED, PROGRAMMABLE, HIGH-THROUGHPUT TISSUE CULTURE AND ANALYSIS SYSTEMS AND METHODS

CROSS-REFERENCE TO RELATED APPLICATIONS

This application is the National Stage of International Application No. PCT/US2019/042295 filed Jul. 17, 2019, which claims the benefit of U.S. Provisional Application No. 62/699,478 filed Jul. 17, 2018. The entirety of each of these applications is hereby incorporated by reference for all purposes.

BACKGROUND

Currently available cell culture and analysis systems are generally either static systems or dynamic systems that use custom-made perfusion (bioreactor) systems. Both of these systems generally require the tissue maintenance, analysis and measurement methods to be performed manually. This can be not only time consuming but can result in highly inconsistent tissue maintenance, measurement, and analysis. Thus, the currently available systems lack adequate reproducibility, aseptic techniques, accuracy, and scalability, to analyze cultures, such as at commercial manufacturing scales.

SUMMARY

Thus, there is need for automatic and efficient technologies that can perform robust and high-throughput analyses using automatic maintenance, monitoring, and analysis.

The devices, systems, and methods are directed to high-throughput, programmable, and fully automatized culture and analysis platforms. For example, this can provide automatic maintenance of the cell/tissue culture (culture media change, perfusion at varying flow rates, etc.), in situ imaging, image (photo/video) analysis.

In some embodiments, the systems may include a culture analysis system. The culture analysis system may include a (tissue/cell) culture device. The culture device may include a cover or lid configured to be secured to a main body. The main body may include one or more chambers configured to hold one or more samples, such as tissue and/or cell sample. In some embodiments, the cover may include one or more regions configured to overlap with the one or more chambers of the main body when the cover is secured to the main body so that each region corresponds to a chamber of the main body. The cover may also include a fluidic pathway disposed in each region and configured be in fluidic communication with a corresponding chamber. Each fluidic pathway may include a fluid inlet and a fluid outlet disposed in each region and is configured to be in fluidic communication with the corresponding chamber. In some embodiments, the cover may also include an optical pathway disposed in each region for the corresponding chamber.

In some embodiments, the culture device may include a multi-well plate and each chamber of the plate may be a well, such as a tissue culture well.

In some embodiments, each optical pathway may include one or more of optical imaging fibers and one or more of illuminating fibers. In some embodiments, the cover may further include one or more groups of one or more sets of optical ports. Each set of optical ports may include a first optical connection port for the one or more optical imaging fibers and a second optical connection port for the one or more illuminating fibers for each region.

In some embodiments, the cover may include one or more groups of one or more sets of fluidic connection ports. Each set of fluidic connection ports may include a first connection port for the fluid inlet and a second connection port for the fluid outlet for each region.

In some embodiments, the cover may include two groups of one or more sets of optical ports and two groups of one or more sets of fluidic connection ports.

In some embodiments, the culture analysis system may further include one or more waste storage containers; one or more media storage containers; and an electronic controller.

In some embodiments, the culture analysis system may further include a control device. The control device may be in fluidic communication with the culture device. In some embodiments, the control device may include one or more groups of one or more sets of fluidic connection ports complimentary to the one or more groups of the one or more sets of fluidic connection ports of the culture device.

In some embodiments, the control device may include a waste removal unit and a media supply unit connected to the one or more waste storage reservoirs and the one or more media storage reservoirs, respectively. The waste removal unit may include a suction pump and one or more valves, and the media supply unit may include an injection pump and one or more valves.

In some embodiments, the control device may include one or more injection valves that is in fluidic communication with the one or more media storage reservoirs and one or more suction valves that is in fluidic communication with the one or more waste storage reservoirs. Each injection valve may be in fluidic communication with a fluid inlet of the cover. Each suction valve may be in fluidic communication with a fluid outlet of the cover. In some embodiments, the electronic controller may be configured to control each valve.

In some embodiments, the control device and/or the cover may include one or more temperature regulation units. The one or more temperature regulation units may include one or more of cooling units, heating units, among others, or a combination thereof.

In some embodiments, the cover may include the one or more waste storage containers, the one or more media storage containers, and the electronic controller. In some embodiments, each region of the cover may include the one or more waste storage reservoirs and the one or more media storage reservoirs.

In some embodiments, the culture analysis system may further include an image acquiring device configured to acquire one or more images of each chamber. The one or more groups of one or more sets of optical ports of the cover may be in communication with the image acquiring device.

In some embodiments, the methods may include a method of performing one or more cell culture analyses. The method may include providing (i) a culture device including a body having one or more chambers in which a sample is disposed and a cover secured to the body, (ii) one or more waste storage reservoirs, and (iii) one or more media storage reservoirs storing one or more media. The cover may include one or more regions that overlaps with the one or more chambers of the body so that each region corresponds to a chamber of the main body. The cover may include one or more fluidic pathways disposed in each region and in fluidic communication with a corresponding chamber. Each fluidic pathway may include a fluid inlet and a fluid outlet. The method may further include causing fluid exchange in the one or more chambers by controlling the fluid flow rate and timing (i) between the inlet of each region corresponding to the one or more chambers and the one or more media storage reservoirs and (ii) between the outlet of each region corresponding to the one or more chambers and the one or more waste storage reservoirs, based on one or more settings.

In some embodiments, the fluid exchange may be automatically and individually controlled for each chamber. In some embodiments, the fluid exchange may be automatically controlled based on one or more stored settings.

In some embodiments, the cover may include an optical pathway disposed in each region for the corresponding chamber. The method may further include acquiring one or more static or dynamic images of the one or more chambers.

In some embodiments, the method may further include determining one or more features using the acquired images of the one or more chambers. The method may further include controlling the fluid exchange for the one or more chambers based on the one or more features.

In some embodiments, the cover and/or a control device may include the one or more waste storage reservoirs and the one or more media storage reservoirs. In some embodiments, each region may include and/or be in fluidic communication the one or more waste storage reservoirs and the one or more media storage reservoirs.

In some embodiments, the cover may include an electronic controller. In some embodiments, the electronic controller of the cover may cause the fluid exchange in the one or more chambers.

In some embodiments, the providing may include connecting the culture device to a control device. The control device may include the one or more waste storage reservoirs, the one or more media storage reservoirs, and the electronic controller. The electronic controller of the control device may cause the fluid exchange.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
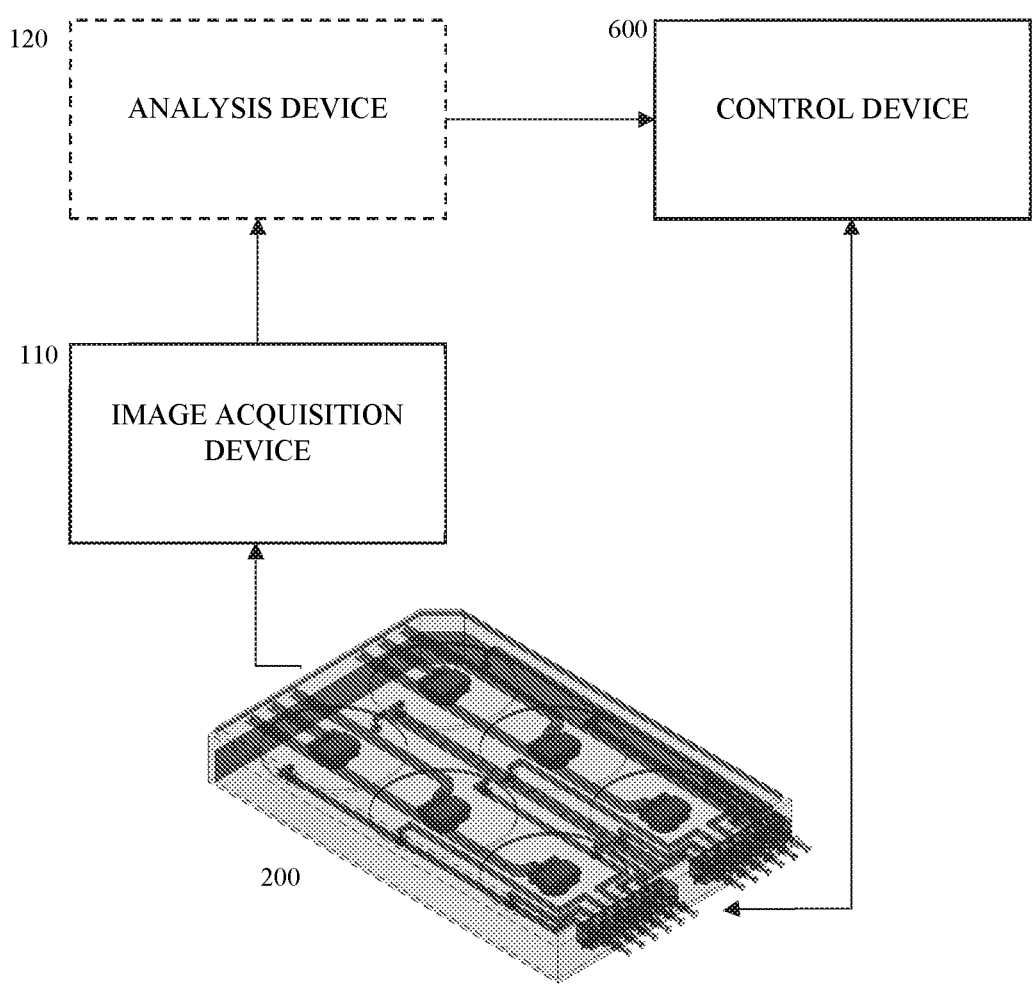
FIG. 1 shows an example of a system for performing culture analyses according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure. Unless otherwise defined herein, scientific and technical terms used in connection with the disclosure shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. As used herein, the term "one or more" such as one or more members of a group of members, can be understood to encompass inter alia a reference to any one of the members, or to any two or more of the members, such as, e.g., any >3, >4, >5, >6 or >7 etc. of the members, and up to all of the members.

The systems and methods of the disclosure can provide programmed and automated conduction of various cellular processes, including multi-step, such as cell differentiation and quantitative assays. The systems and methods can utilize disposable culture lids or covers that are designed for varying sizes of conventional tissue/cell culture devices (e.g., plates), and that enable media exchange for each chamber, such as each well, of a culture device. In some embodiments, the lids or covers can enable imaging exchange for each chamber/well of a culture device. By placing the fluidic and imaging pathways in the lids or covers, the systems of the disclosure can be cost effective.

In some embodiments, the systems and methods of the disclosure can utilize a control device connected to the lid and/or embedded in the lid that stores and dispenses culture media/reagents to the culture device via the lid, which can be automated based on user or stored programmed settings. In some embodiments, the systems and methods can further utilize an analysis device that can communicate with the lid and the control device, and that can analyze imaging data of the cells being cultured in the culture device acquired by an imaging acquiring device (e.g., a camera). The analysis device can communicate the analyses to the control device to control the culture processes performed in the culture device by controlling the fluidic and imaging pathways provided in the lid. In some embodiments, the system may be closed loop and the imaging analysis may be used as feedback signaling to control the fluidic and imaging operations, thereby optimizing tissue maturation and functionality. Thus, by providing programmed and automated maintenance of the cell cultures, in-situ imaging and imaging analyses, the systems and methods according to the disclosure can enable a cost-effective, high-throughput, programmable, fully automatized culture and analysis.

The systems and methods according to the disclosure can refill the culture media storage reservoir (and emptying the waste media storage), as well as acquire images, while the culture is ongoing without disrupting the tissue culture. This can allow using this system for automated cell culture for unlimited time durations.

In some embodiments, the systems and methods of the disclosure can be used to analyze and optimize the culture process of a wide variety of samples, such as bioengineered tissues and organs, in a fully automated and programmable manner. By way of example, the systems and methods can provide a highly scalable solution to in situ analysis of tissue cultures and can be used for conducting static and dynamic cultures (i.e., perfusion bioreactor system). The systems and methods of the disclosure can also provide in situ imaging capabilities without disturbing 2D or 3D tissue constructs.

In some embodiments, the systems and methods of the disclosure can be utilized for high-throughput drug screening in a fully automated and programmable manner. By of example, the in situ imaging system according to the disclosure may be used for capturing fluorescence signal of cells during the culture for live, fluorescently tagged cells. In another example, the systems and methods of the disclosure can be used to perform immunohistochemical analysis of cell cultures at pre-defined time points in culture, followed by imaging and image analyses.

In some embodiments, the systems and methods of the disclosure can also be utilized as a high-throughput, programmable bioreactor, providing dynamic culture conditions at varying flow rates and regimens.

FIG. 1 shows an example of a culture system 100 according to some embodiments. In some embodiments, the system 100 may include one or more culture devices 200 in which the cellular processes can be performed on a sample and a control device 600 configured to store and control the flow of culture media into and out of the culture device(s) 200. In some embodiments, the system 100 may further include an image acquisition device 110, such as a CCD/CMOS camera, configured to acquire static or dynamic images of the sample being cultured within the culture device(s) 200. In some embodiments, the system 100 may further include an analysis device 120 configured to receive and process the image data of the sample disposed in the culture device 200 from the image acquisition device 110 so as to control the control device 600 and its processes performed in the culture device 200.

In some embodiments, one or more modules of the control device 600 and/or the analysis device 120 may be included in either module of the system 100 and another module of the system 100, such as the device 200. In some embodiments, the image acquisition device 110 and/or analysis device 120 may be omitted.

Figure 2:
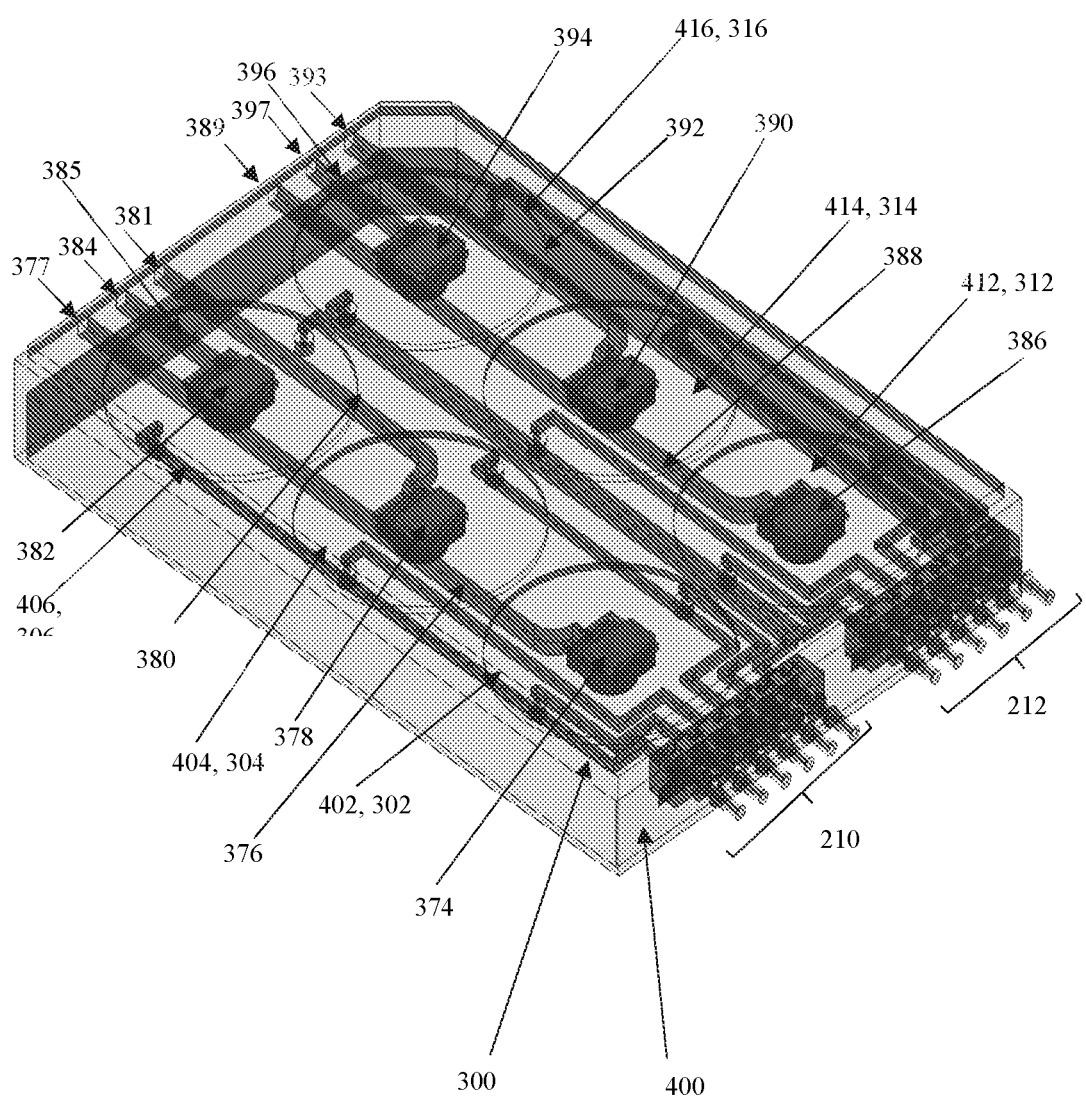
FIG. 2 shows a perspective view of an example of a culture device according to embodiments.
Figure 3:
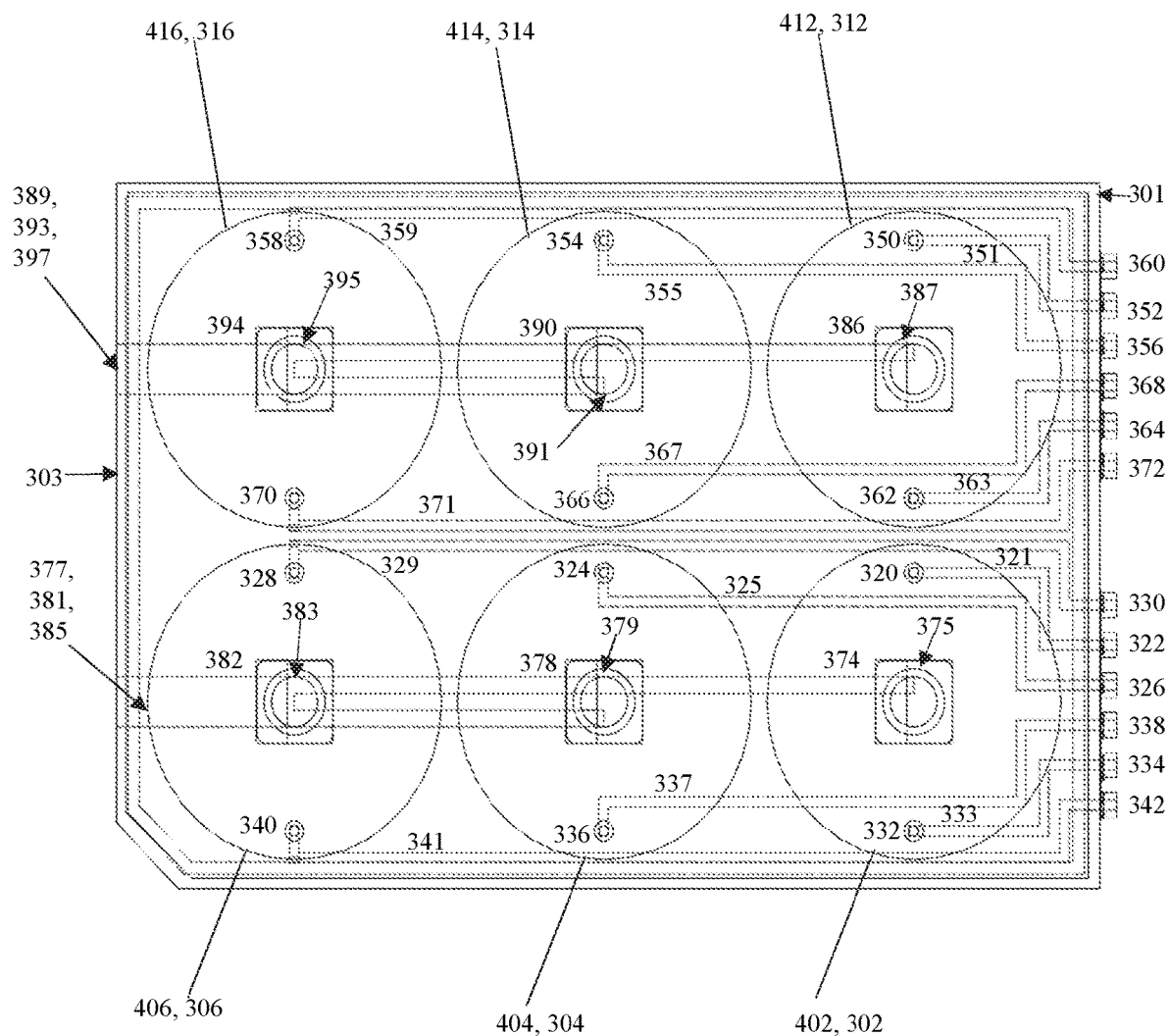
FIG. 3 shows a top view of the culture device shown in FIG. 2.
Figure 4:
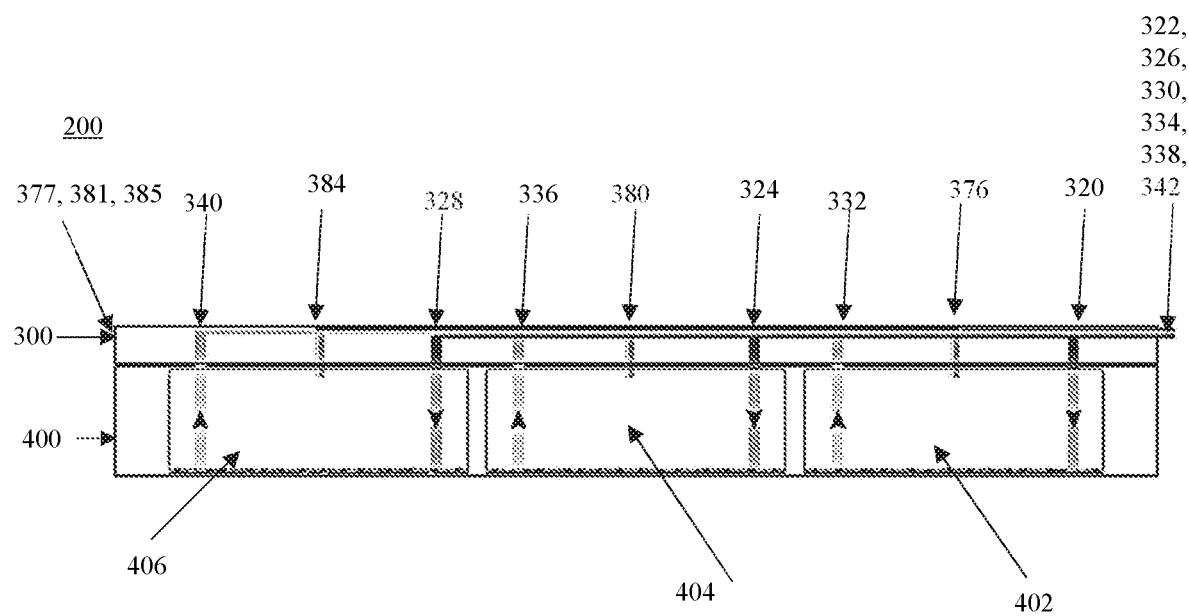
FIG. 4 shows a side view of the culture device shown in FIG. 2.

FIGS. 2-5 and 9 show examples of a culture device according to embodiments. As shown in FIG. 2-4, the device 200 may include a lid or cover member 300 that is configured to fit onto a top of a culture body (also referred to as "body") 400 that is configured to hold one or more samples. In some embodiments, the cover 300 may include a fluidic pathway. The fluidic pathway may include one or more ports and fluidic channels for directing flow of media into and out of the chamber(s) of the body 400. In some embodiments, the cover 300 may also include an imaging or optical pathway. The imaging or optical pathway of the cover 300 may include one or more ports and channels for directing imaging and/or optical capabilities, for example, imaging and/or optical fibers, into and out of the chamber(s) of the body 400.

The cover member 300 may be structured to fit on any available culture vessel. In some embodiments, the body 400 may include any cell or tissue culture vessel including but not limited to plates, such as microtiter plates, or multi-well plates or microplates, dishes, such as petri-dish, culture flasks, culture bottles, among others, or a combination thereof. The body 400 may include one or more chambers configured to hold one or more samples on which the processes are to be performed. In some embodiments, the one or more samples may include but is not limited to any biological sample (e.g., cell, tissues, their products, etc.), among others, or a combination thereof.

In some embodiments, the chamber may be in a form of a well. In the example shown in FIGS. 2-4, the body 400 may be a multi-well plate in form of a flat plating having six chambers in form of (circular) wells. As shown in FIG. 2, the body 400 may include six chambers 402, 404, 416, 412, 414 and 416 disposed in two rows. However, the body 400 is not limited to a six well plate and may be any available cell culture vessel that includes less or more chambers. For example, the body 400 may include but is not limited to a well plate having 12, 24, 48, 96 and 384 number of well plates.

In some embodiments, the cover member 300 may include one or more regions that correspond to the one or more chambers of the body 400 so that when the cover member 300 is secured to the body 400 the one or more regions of the cover member 300 overlap with the one or more chambers of the body 400. The number of regions of the cover member 300 and the number of the chambers of the body 400 may be the same. As shown in FIGS. 2 and 3, the cover member 300 may include six regions 302, 304, 306, 312, 314, and 316 that are disposed in two rows and that overlap with the six chambers 402, 404, 406, 412, 414 and 416, respectively, of the body 400.

In some embodiments, the cover member 300 may include a plurality of channels that are directly machined or embedded inside. Each channel may have openings at each end. "Channels" can be pathways (whether straight, curved, single, multiple, in a network, etc.) disposed within or through the cover member 300 (e.g., silicon, plastic, etc.) that allow for movement of liquids and gasses (also referred to as "fluidic channels"), movement of data/signals (e.g., imaging/optical data, imaging/optical signals, etc.), among others, or a combination thereof. Channels thus can connect other components, i.e., keep components "in communication" and more particularly, "in fluidic communication." As used herein, the terms "linked," "connected to," "coupled to," "in contact with" and "in communication with" may refer to any form of interaction between two or more entities, including mechanical, electrical, magnetic, electromagnetic, fluidic, and thermal interaction and does not exclude the presence of intermediate components such that two components may be coupled to each other even though they are not in direct contact with each other. For example, two components may be coupled to each other through an intermediate component (e.g. tubing or another conduit).

In some embodiments, the fluidic channels may have various geometries to facilitate a wide range of flow rates through the channels of liquids, gases, among others, or a combination thereof. By way of example, the fluidic channels may be microchannels (e.g., channels with dimensions less than 1 millimeter and greater than 1 micron).

In some embodiments, the cover member 300 may include a set of channels disposed for each region so that each set communicates with a respective chamber of the body 400. The set of channels may include a set of fluidic channels. This way, each chamber of the body 400 may communicate with a set of individual (fluidic) channels for fluid exchange disposed within the cover member 300. In some embodiments, the set of (fluidic) channels (also referred to as "fluidic pathways") may include one or more inflow channels (also referred to as "fluid inlet" or "inlet") and one or more outflow channels (also referred to as "fluid outlet" or "outlet"). The inflow channel(s) may be configured to deliver or inject media from one or more media storage reservoirs to the respective chamber and the outflow channel(s) may be configured to remove or suction media from that chamber to be delivered to one or more waste storage reservoirs. The cover member 300 may include any number of inflow and outflow channels for each region/chamber and are not limited to the one inflow channel and one outflow channel for each region/chamber as shown in FIGS. 2 and 3.

In some embodiments, each inflow channel may include (i) a first end disposed within the region and in fluidic communication with the corresponding chamber; (ii) a second end disposed at a side of the cover member 300 and in fluidic communication with one or more media storage reservoirs; and (iii) a length therebetween. The first end of each inflow channel may be an inlet. In some embodiments, each outflow channel may include (i) a first end disposed within each region and in fluidic communication with the chamber; (ii) a second end disposed at a side of the cover member 300 and in fluidic communication with one or more waste storage reservoirs; and (iii) a length therebetween. The first end of each outflow channel may be an outlet. In some embodiments, the cover member 300 may include a connection port disposed at the second end of each inflow and outflow channel.

By way of example, as shown in the top view shown in FIG. 3, the device 200 may include six sets of fluidic channels or pathways disposed within each region of the cover 300 that is in fluidic communication with the corresponding chamber. This way, the fluidic pathways may be individually controlled for each region/chamber, for example, by the control device 600

In some embodiments, the cover member 300 may include:

for region 302, (i) an inflow channel 321 that extends between an inlet 320 disposed in the region 302 and a port 322 disposed on a side 301 of the cover member 300 and (ii) an outflow channel 333 that extends between an outlet 332 disposed in the region 302 and a port 334 disposed on the side 301 of the cover member 300;

for region 304, (i) an inflow channel 325 that extends between an inlet 324 disposed in the region 304 and a port 326 disposed on the side 301 of the cover member 300 and (ii) an outflow channel 337 that extends between an outlet 336 disposed in the region 304 and a port 338 disposed on the side 301 of the cover member 300;

for region 306, (i) an inflow channel 329 that extends between an inlet 328 disposed in the region 306 and a port 330 disposed on the side 301 of the cover member 300 and (ii) an outflow channel 341 that extends between an outlet 340 disposed in the region 306 and a port 342 disposed on the side 301 of the cover member 300;

for region 312, (i) an inflow channel 351 that extends between an inlet 350 disposed in the region 312 and a port 352 disposed on the side 301 of the cover member 300 and (ii) an outflow channel 363 that extends between an outlet 362 disposed in the region 312 and a port 364 disposed on the side 301 of the cover member 300;

for region 314, (i) an inflow channel 355 that extends between an inlet 354 disposed in the region 314 and a port 356 disposed on the side 301 of the cover member 300 and (ii) an outflow channel 367 that extends between an outlet 366 disposed in the region 314 and a port 368 disposed on the side 301 of the cover member 300; and for region 316, (i) an inflow channel 359 that extends between an inlet 358 disposed in the region 316 and a port 360 disposed on the side 301 of the cover member 300 and (ii) an outflow channel 371 that extends between an outlet 370 disposed in the region 316 and a port 372 disposed on the side 301 of the cover member 300.

In some embodiments, the ports may be disposed in one or more groups. In some examples, the number of rows of chambers may correspond to the number of groups of ports. As shown in FIG. 3, the cover member 300 may include two groups of ports. In some embodiments, each group of ports may be configured to receive a complimentary connection member for connecting the device 200 to the control device 600 via the cover member 300 using a conduit, such as tubing. As shown in FIG. 2, the group of the ports 322, 326, 330, 334, 338, and 342 may be configured receive a connection member 210 and the group of the ports 352, 356, 360, 364, 368, and 372 may be configured to receive a connection member 212.

FIG. 4 shows a side view of the device 200 (i.e., the cover member 300 attached to the body 400) showing an example of the fluidic operation (e.g., when the device 200 is attached to the control device 600). As shown in this example, the inlet and inflow channel of each region can act as an injection channel to inject a media into the respective chamber. The outlet and outflow channel of that region can act as a suction channel to suction or remove media from the respective chamber.

In some embodiments, the cover member 300 may include an optical pathway disposed in each region for each corresponding chamber. In some embodiments, the optical pathway may include a set of one or more optical fibers for each region. In some embodiments, the set of optical fibers may include one or more imaging optical fibers, one or more illuminating optical fibers, among others, or a combination thereof.

In some embodiments, the one or more imaging optical fibers may be configured to capture static optical images of the sample inside each respective chamber, dynamic optical images (e.g., video) of the sample inside each respective chamber, among others, or a combination thereof. The one or more imaging optical fibers may be connected or coupled to an image acquisition device, such as the image acquisition device 110, for acquiring images of the sample inside each respective chamber.

In some embodiments, the one or more illuminating optical fibers may be configured to emit light into the respective chamber when the image is acquired by an optical image acquisition device, such as the optical image acquisition device 110. In some embodiments, the one or more illuminating optical fibers may be connected or coupled to a light source, including but not limited to a laser diode, a light emitting diode device, a fiber optic light source, an infrared light source, a visible light source, an ultraviolet light source, among others, or a combination thereof.

In some embodiments, each set of one or more optical fibers for each region may extend between a detection or optical window disposed within each region to optical ports disposed on a side of the cover member 300. In some embodiments, the detection or optical window may be in the center of each region and/or disposed in each region so as to be disposed in the center of the corresponding chamber. In some embodiments, the side of the cover member 300 on which the optical ports may be disposed may be different from the side of the cover member 300 on which the fluid ports may be disposed.

In some embodiments, the optical pathway may further include one or more optic lenses. In some embodiments, the one or more optical lenses may be disposed in the detection or optical window. The one or more optical lenses may include but are not limited to a magnification lens.

The optical pathway can allow for in situ imaging. By placing one or more optical fibers in the center of each well, imaging the cell culture can be performed based on a pre-defined schedule, in a fully automated manner that will not disturb the sample (e.g., cells) being cultured. The imaging can be done in bright field and/or fluorescence modes.

By way of example, as shown in the top view shown in FIG. 3, the device 200 may include six sets of optic or imaging pathways disposed within each region of the cover 300 that extend between a side of the cover 300 an optical or detection window disposed substantially in the center of the region. This way, the imaging can be acquired with respect to the center of the corresponding chamber and the optical pathways may be individually controlled for each region/chamber.

In some embodiments, as shown in FIGS. 2 and 3, the cover member 300 may include:

for region 302, a set of optical fibers 376 that includes one or more of the optical imaging fiber(s) and optical illuminating fiber(s) that extends between a detection window 374 disposed in the region 302 and a port 377 disposed on a side 303 of the cover member 300;

for region 304, a set of optical fibers 380 that includes one or more of the optical imaging fiber(s) and optical illuminating fiber(s) that extends between a detection window 378 disposed in the region 304 and a port 381 disposed on the side 303 of the cover member 300;

for region 306, a set of optical fibers 384 that includes one or more of the optical imaging fiber(s) and optical illuminating fiber(s) that extends between a detection window 382 disposed in the region 306 and a port 385 disposed on the side 303 of the cover member 300;

for region 312, a set of optical fibers 388 that includes one or more of the optical imaging fiber(s) and optical illuminating fiber(s) that extends between a detection window 386 disposed in the region 312 and a port 389 disposed on the side 303 of the cover member 300;

for region 314, a set of optical fibers 392 that includes one or more of the optical imaging fiber(s) and optical illuminating fiber(s) that extends between a detection window 390 disposed in the region 314 and a port 393 disposed on the side 303 of the cover member 300; and for region 316, a set of optical fibers 396 that includes one or more of the optical imaging fiber(s) and optical illuminating fiber(s) that extends between a detection window 394 disposed in the region 314 and a port 397 disposed on the side 303 of the cover member 300.

In some embodiments, as shown in FIGS. 2 and 3, the cover member 300 may further include one or more optic lens disposed in each optic window for each region. In some embodiments, the cover member 300 may include an optic lens 375 disposed in the optic window 374 of the region 302; an optic lens 379 disposed in the optic window 378 of the region 304; an optic lens 383 disposed in the optic window 382 of the region 306; an optic lens 387 disposed in the optic window 386 of the region 312; an optic lens 391 disposed in the optic window 390 of the region 314; and an optic lens 395 disposed in the optic window 394 of the region 316.

In some embodiments, the optical ports may be disposed in one or more groups. In some examples, the number of rows of chambers may correspond to the number of groups of ports. As shown in FIG. 3, the cover member 300 may include two groups of optical ports. In some embodiments, each group of ports may be configured to receive a complimentary connection member for connecting the device 200 to an image acquisition device 110 via the cover member 300, using a conduit (e.g., optic fibers/cables). As shown in FIG. 3, the group of the ports 377, 381, and 385 may be configured receive a connection member (not shown) for connecting to an image acquisition device and/or light source, and the group of the ports 389, 393, and 397 may be configured to receive another connection member (not shown) for connecting to the image acquisition device and/or light source.

In some embodiments, the cover member 300 may be connected to the image acquisition device 110 and/or a light source using one or more optical multiplexers.

As shown in FIGS. 2 and 3, the optical ports may be disposed on the side 303 of the cover member 300 which opposes the side 301 of the cover member 300 on which the fluid ports are disposed. In some embodiments, the optical ports and the fluid ports may be disposed on different sides. In some embodiments, the ports may be disposed on the same side.

In some embodiments, the cover member 200 may omit one or more members of the optical pathway. In some embodiments, the cover member 200 may omit the entire optical pathway.

In some embodiments, the inlet and the outlet may be disposed on opposing sides or corners of the respective region. In some embodiments, the inlet and outlet may be disposed within the respective region on opposing sides with respect to the detection window.

In some embodiments, the cover member 300 may include less ports. By way of example, the cover member 300 may include a single connection port for the inflow channels and a single connection port for the outflow channels so that the cover member 300 has one inflow connection port and one outflow connection port for the entire cover member. For example, the inflow channels for the regions may combine or merge into a single channel having a single connection port and the outflow channels for the regions may combine or merge into a single channel having a single connection ports.

Figure 5:
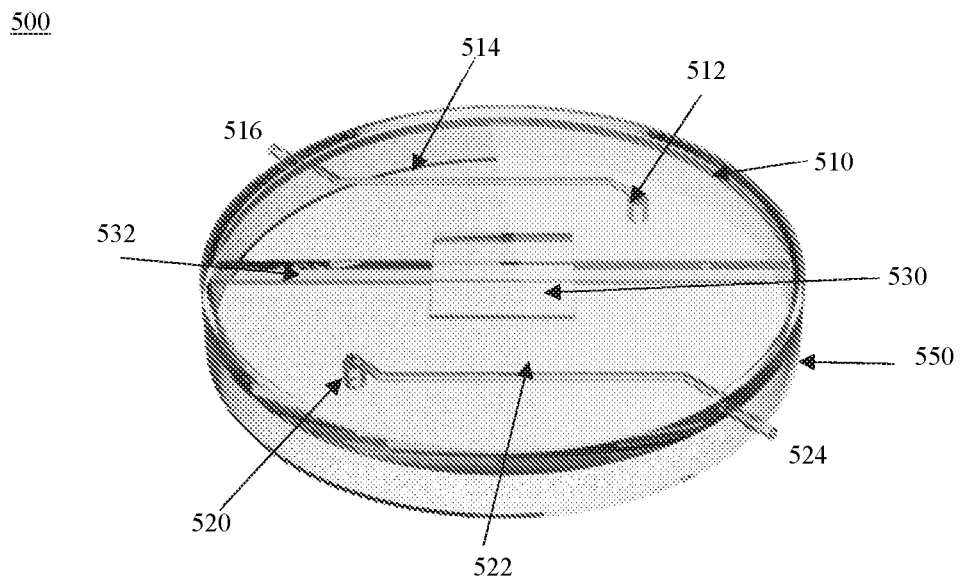
FIG. 5 shows an example of another culture device according to embodiments.

In some embodiments, the device 200 may have a different shape. By way of example, the cover member may have a shape specific to a different culture vessel so that the resulting device may have a different shape. For example, FIG. 5 shows an example of a device 500. In this example, the device 500 may include a cover member 510 having a round shape that can properly secure to a round body 550, which is an example of a round petri-dish. In this example, the body 550 has one culture chamber so that the cover 510 has one corresponding region. Like the cover member 300, the cover member 510 may include an inflow channel 514 that extends between an inlet 512 and a port 516 and an outflow channel 522 that extends between an outlet 520 and a port 524 Also, like the cover member 300, the cover member 510 may also include an optical pathway. As shown in FIG. 5, the cover member 510 may include an optical lens 530 disposed in an optical window and a set of optical fibers 532 that extend between sides of the cover member 510 and along the optical window.

In some embodiments, the cover member 300 may be reusable. For example, the cover member 300 may be washed and sterilized after each use. Also, because the cover member 300 does not include pump(s), the cover members 300 according to the disclosure can have a lower chance of failure.

In some embodiments, more than one device 200 may be connected to the control device 600 and/or the image acquisition device 110 and/or the analysis device 200. For example, two or more devices 200 may be stacked and maintained in a culture incubator. In another example, two or more devices 200 may be positioned side by side and maintained in a culture incubator.

Figure 6:
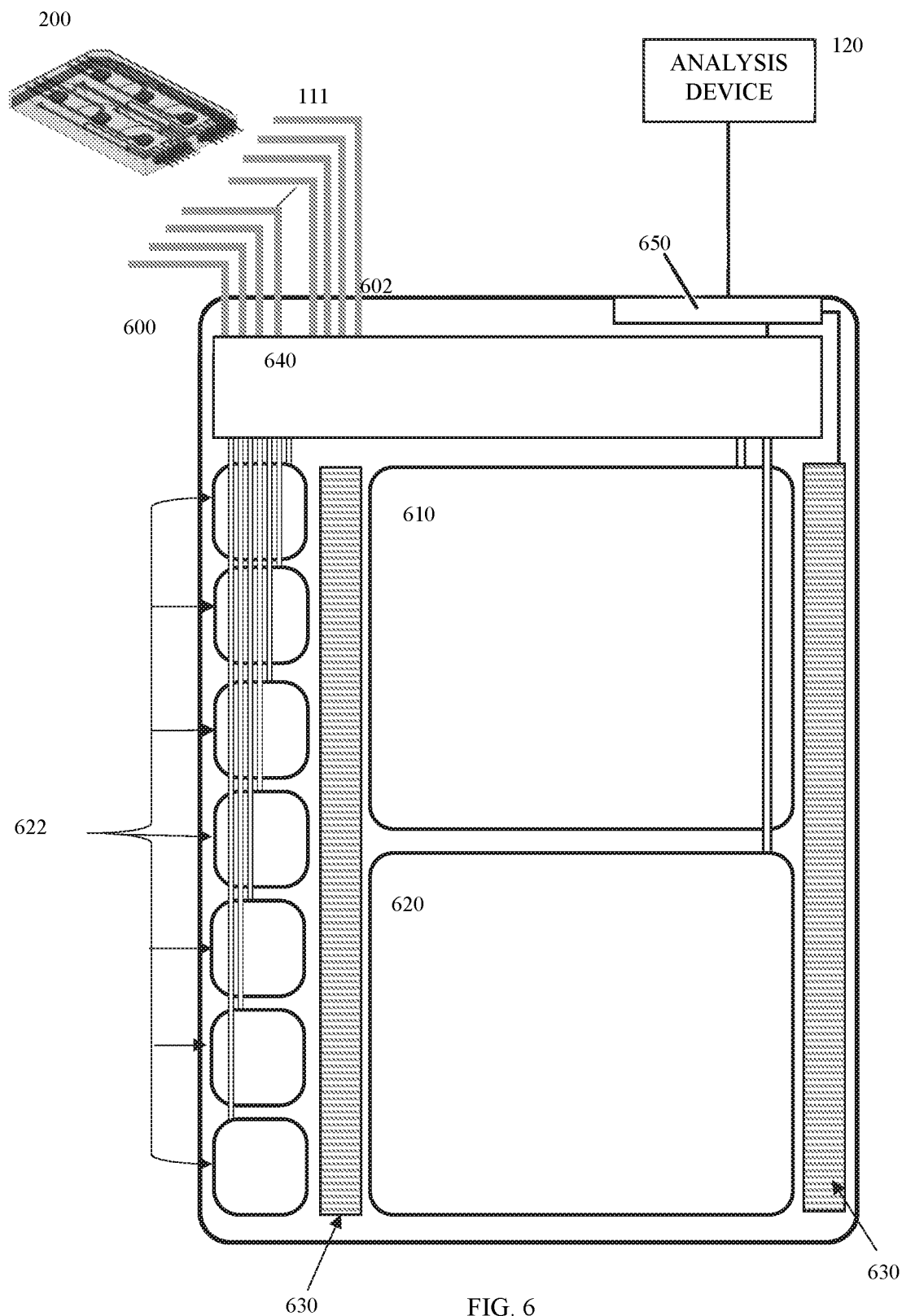
FIG. 6 shows an example of a control device according to embodiments.

FIG. 6 shows an example of a schematic of the control device 600 according to embodiments. In some embodiments, the control device 600 may be in fluidic communication and connection with the device 200 via the connection ports of the cover member 300 and conduit(s). In some embodiments, the control device 600 may be wired or wirelessly connected to the analysis device 120.

In some embodiments, the control device 600 may include one or more waste storage reservoirs 610 to collect the media retrieved from the device 200, one or more media storage reservoirs 620, 622 storing one or more media to be delivered to the device 200, an electronic controller 650, and one or more fluid (exchange) control members 640. In some embodiments, the control device 100 may also include one or more temperature control members 630. Although not shown, the control device 600 may include additional electrical and/or mechanical components, such as one or more sources of power (e.g., electrical energy), sensors (e.g., temperature, flow (e.g., to detect errors along the fluidic pathway, etc.), among others, or any combination thereof. The control device 600 may include one or more ports 602 for connecting to the fluid connection ports of the cover member 300, via the connections 210 and 212, for example, using connection members 111, such as tubing.

In some embodiments, the control device 600 may include a main media storage reservoir 620. In some embodiments, the control device 600 may also include one or more additional media storage reservoirs 622. In some embodiments, the one or more additional media storage reservoirs 622 may be smaller than the main media storage reservoir 620. The one or more storage reservoirs 620 and/or 622 may include media including but not limited to any reagent, solutions (e.g., fixative solutions (e.g., fixative solutions (e.g., paraformaldehyde) and staining solutions (fluorescently tagged antibodies)) etc.), materials that include gasses (e.g., oxygen, carbon dioxide, etc.), among others, or any combination thereof. For example, the one or more additional media storage reservoirs 622 may store quantities of other fluid reagents that can be used for cell culture assays such as specific culture media or reagents for cell viability and proliferation assays. In another example, the one or more additional media storage reservoirs 622 may store fixative solutions (e.g., paraformaldehyde) and staining solutions (fluorescently tagged antibodies) that can be used to fix and stain cells at pre-defined time points in the culture process, followed by imaging and image analysis. This can enable capturing fluorescence signal of cells during culture for live, fluorescently tagged cells.

In some embodiments, the waste storage reservoir(s) 610 may be configured to store the media that has been removed or sucked from the chambers of the device 200 using the fluid control members 640.

In some embodiments, the one or more temperature control members 630 may include one or more of temperature control units, such as a cooling unit (e.g., a refrigeration unit), a heating unit, or a combination thereof.

The electronic controller 650 may include a processor and a memory. The controller 650 may be configured to control the fluid control members 640 according to stored settings (e.g., according to a stored program and/or user selected settings), instructions received from the analysis device 110, among others, or a combination thereof. For example, the controller 650 may cause suction and delivery functions by activating the respective pumps and/or valves, to thereby activate and initiate fluid exchange between the device 200 and the control device 600. In some embodiments, the controller 650 may be configured to control the temperature control unit 630 to maintain the temperature according to the stored settings.

In some embodiments, the fluid control members 640 may include one or more injection actuators (e.g., pumps), one or more suction actuators (e.g., pumps), one or more valves (e.g., electronic microvalves), among others, or a combination thereof. The fluid control members 640 may be controlled by the controller 650. In some embodiments, the one or more injection pumps may be any injection pump, for example, any dynamic or displacement pump, such as a syringe pump, peristaltic pump, among others, or a combination thereof. In some embodiments, the one or more suction pumps may be any suction/vacuum pump, for example, any dynamic or displacement pump, such as a syringe pump, peristaltic pump, among others, or a combination thereof.

In some embodiments, the fluid control members 640 may include an injection actuator (e.g., pump) to cause delivery of a media from the one or more media storage units 620, 622 to one or more chambers and a suction actuator (e.g., pump) to cause removal or suction of a media from one or more chambers to the waste storage reservoir(s) 610. The fluid control members 640 may also include one or more electronic microvalves. Each pump may be connected to the conduits (e.g., tubes) 611 via the electronic microvalves. The controller 650 may control the valves to control the injection and/or removal of the media for each region individually. This way, the injection actuator and valves may act as a media supply unit and the suction actuator and the valves may act as a media or waste removal unit.

Figure 7:
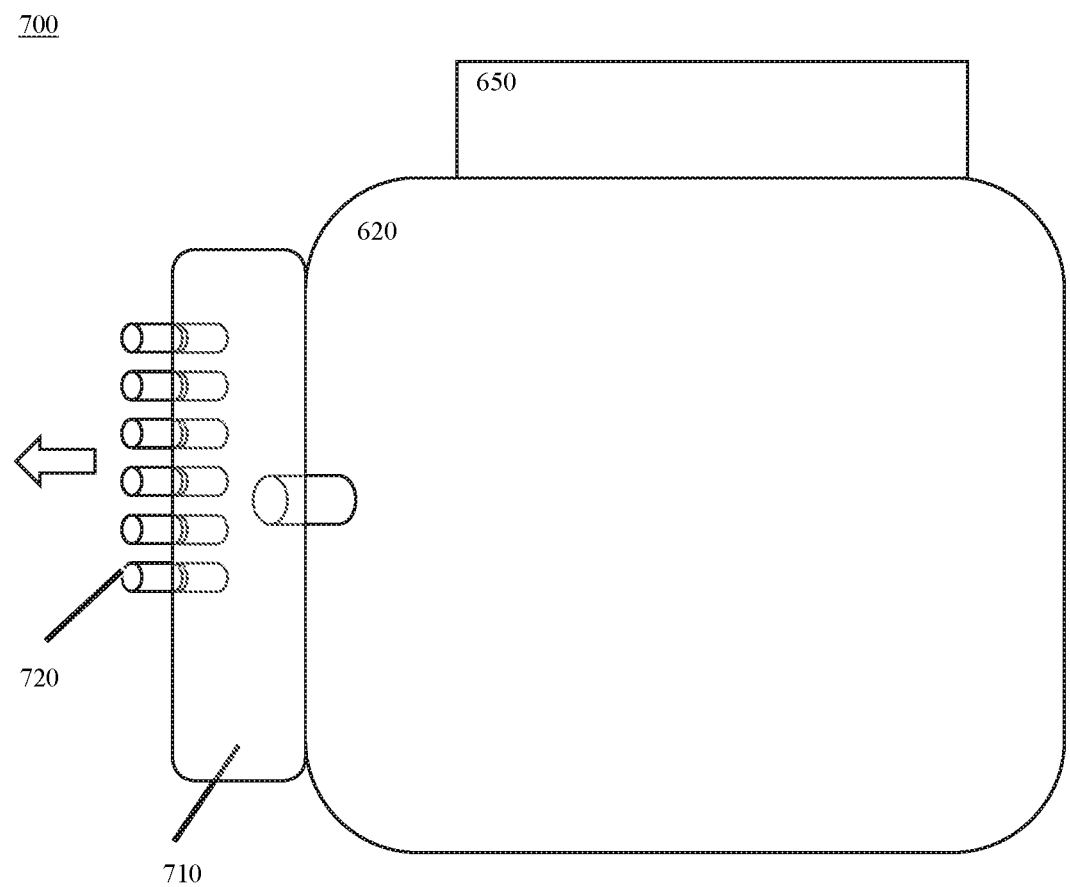
FIG. 7 shows an example of a media supply unit according to embodiments.
Figure 8:
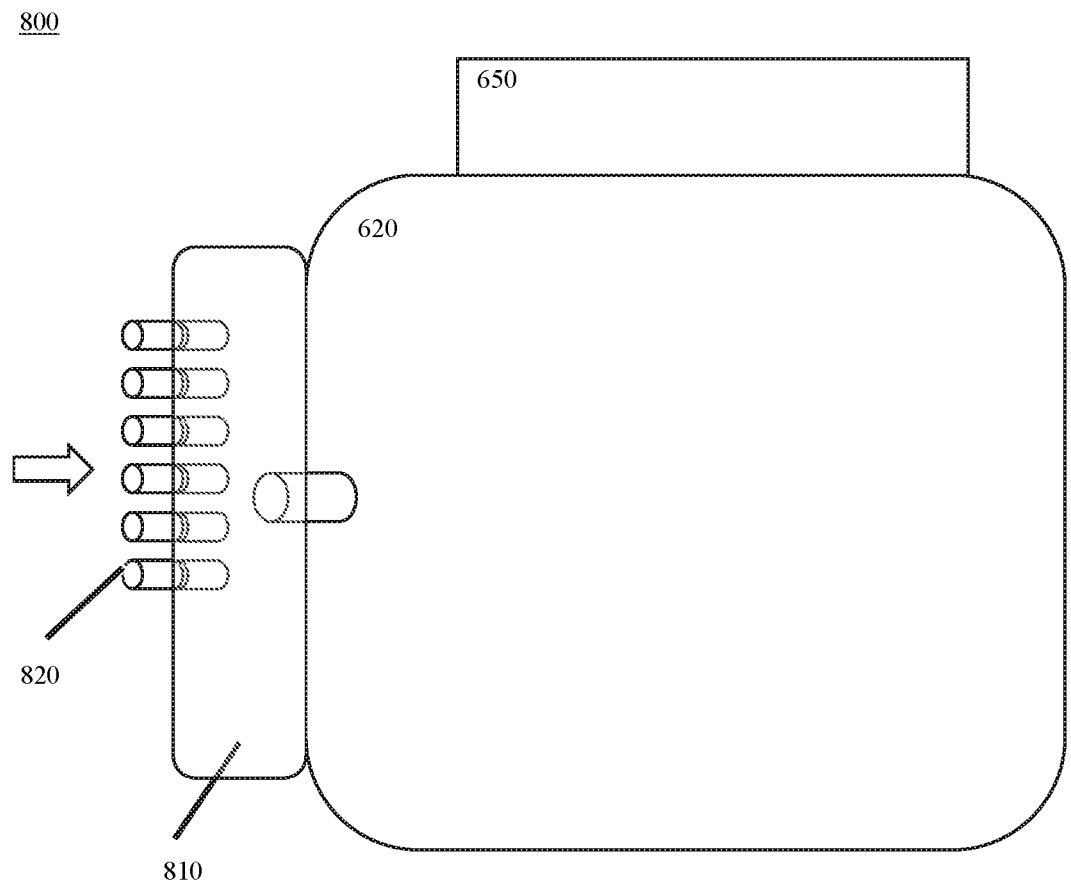
FIG. 8 shows an example of a waste removal unit according to embodiments.

In some embodiments, the injection actuator and/or the suction actuator may be disposed outside of the control device 600 and connected to the respective reservoir. FIGS. 7 and 8 show examples 700 and 800 of a media supply unit and a waste removal unit, respectively, according to embodiments.

As shown in FIG. 7, the media storage reservoir(s) (e.g., 620) can be pressurized, for example, with positive pressure, using a pump 710. In this example, the media storage reservoirs (e.g., 620) can be directly connected to the valves 720. This way, when the controller 650 activates the valves, the positive pressure can cause the direct transfer of the media (e.g., fluid) from the reservoir(s) (e.g., 620) to the respective chamber of the body 400 via the respective inlet of the cover member 300.

As shown in FIG. 8, the one or more waste storage reservoirs (e.g., 610) can be pressurized, for example, with negative pressure, using a pump 810. In this example, the waste storage reservoir(s) 610 can be directly connected to the valves 820. This way, when the controller 650 activates the valves, the negative pressure can cause the direct transfer of the fluid/media from the respective chamber of the body 400 via the respective outlet of the cover member 300 to the waste storage reservoir(s) 610.

Figure 9:
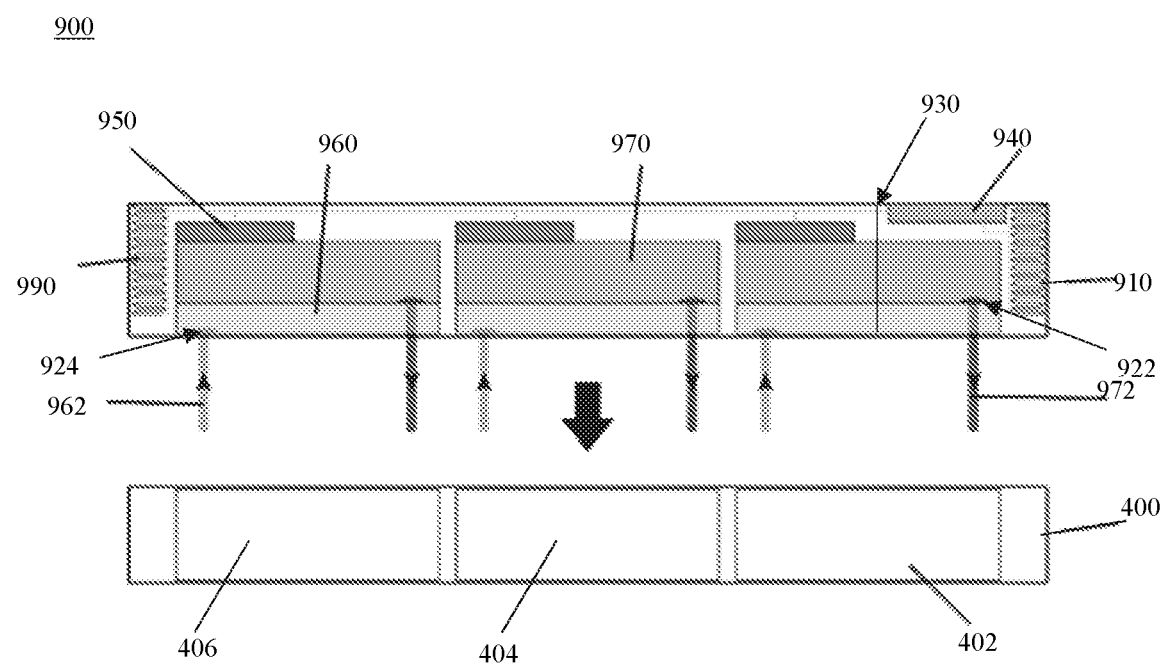
FIG. 9 shows another example of a culture device according to embodiments.

In some embodiments, the cover member 300 may include one or more components of the control device 600. This way, the cover member 300 may be self-sustained, programmable tissue culture unit. FIG. 9 shows an example of a device 900 that includes a cover member 910 configured to fit onto a top of the body 400 that is configured to hold one or more samples.

As shown in FIG. 9, like the cover member 300, the cover member 910 may include an inlet 922 and an outlet 924 for each region. The cover member 910 may also include an optical pathway (e.g., optical components) 930 like the cover member 300. In some embodiments, the cover member 910 may be configured to connect to an image acquisition device 110 and/or the analysis device 120.

In some embodiments, the cover member 910 may include an electronic controller 940 and one or more temperature control members 990. In some embodiments, the cover member 910 may also include one or more of waste storage reservoirs 960, one or more media storage reservoirs 970, and one or more fluid control members 950. In some embodiments, the one or more of waste storage reservoirs 960, the one or more media storage reservoirs 970, and the one or more fluid control members 950 may be disposed in each region as shown in FIG. 9 so that each chamber can be individually cultured/controlled. As shown in FIG. 9, the controller 940 can control the one or more fluid control members 950 to cause a delivery of a media 972 from the media storage reservoir 970 via an inlet 922 to a chamber and cause the removal or suction of a media 962 from the chamber to the waste storage reservoir 964.

In some embodiments, the cover member 910 may include one or more fluid control members 950 for all regions of the cover member 910. For example, if the cover member 910 includes one central pump and a set of valves, the electronic controller 940 can command when the valves will open and close to direct flow in each chamber.

In some embodiments, the cover member may include one or more of waste storage reservoirs, the one or more media storage reservoirs and the one or more fluid control members for all regions so that the fluid exchange for the chambers can be uniformly controlled.

The analysis device 120 may act as a user interface or device configured to control the control device 600 and/or the cover member 300 and/or the cover member 910. In some embodiments, any of the devices of the system 100 may include a non-transitory computer-readable medium storing program instructions thereon that is operable on a user device. A user device may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, or any combination thereof, including the accessories and peripherals of these devices, or any combination thereof. FIG. 5 shows an example of a user device.

In some embodiments, the analysis device 120 may be configured to analyze the acquired image data of each chamber to assess the status of cell culture in each chamber. For example, the analysis device 120 may be configured to determine one or more features or parameters based on the image data. The one or more features or parameters may include but are not limited to cell viability, migration, change of morphology, change of function (e.g., beating rate, contraction velocity, etc. for cardiomyocytes), and cell size. Based on that assessment, the analysis device 120 may provide instructions to the control device 600 and/or the controller 940 to release a specific volume of culture media at a specific time point from the one or more media storage reservoirs.

For example, this can allow for controlling cells confluency, morphology, and function (e.g., contractile behavior in cardiac myocytes) and switching the type of culture media at different times. This can thereby allow for conducting more complex cell cultures including stem cell differentiation protocols (e.g., differentiation of induced pluripotent stem cells to cardiomyocytes which requires switching to different media depending on the stem cell confluency and morphology).

Figure 10:
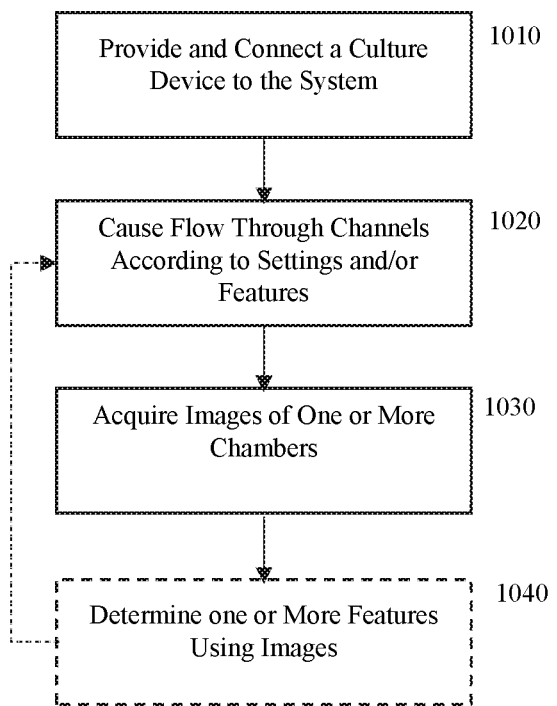
FIG. 10 shows a method of performing one or more culture analyses using the system according to embodiments.

FIG. 10 shows a method 1000 of operating the culture device 200 and/or 900, for example, using one or more components of the system 100. Unless stated otherwise as apparent from the following discussion, it will be appreciated that terms such as "updating," "modifying," "constructing," "generating," "determining," "displaying," "obtaining," "processing," "computing," "selecting," "receiving," "detecting," "estimating," "calculating," "quantifying," "outputting," "acquiring," "analyzing," "enabling," "retrieving," "inputting," "assessing," "performing," "causing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 11. Other systems may also be used.

The method of the disclosure is not limited to the steps described herein. The steps may be individually modified (e.g., including adding additional steps) and/or omitted. It will be also understood that at least some of the steps may be performed in parallel.

In some embodiments, the method 1000 may include a step 1010 of providing a culture device for analysis. For example, the step 1010 may include connecting the culture device 200 or 900 holding one or more samples in one or more chambers to the control device 600. The step 1010 may also include connecting the culture device 200 or 900 to the image acquisition device 110 and/or the analysis device 120.

In some embodiments, the providing step 1010 may include preparing the culture device. In one example, the user can load the culture media or other fluid reagents of interest in the one or more media storage reservoirs 620, 622 of the control device 600 and/or in each media storage reservoir 970 of the cover 910. The user can seed a sample within each chamber of the body(s) 400 and cover each body 400 with the cover member 300 or 910. The devices 200 or 900 may be then placed in an incubator. If more than one device 200 or 900, the devices can be stacked. After which, the device 200 or 900 may be connected to the control device 600, if desired. In some examples, the device 200 or 900 may also be connected to the image acquisition device 110 and/or analysis device 120. In some embodiments, the step 1010 may include calibrating the system 100.

In some embodiments, the one or more fluid ports of the cover member and the corresponding ports of the control device 600 may be color-coded so as to ensure proper connection, for example, for incoming and outcoming flow.

In some embodiments, the step 1010 may include the user providing settings or selecting stored settings for the one or more analyses to be automatically performed to the control device 600 and/or the cover member 300, 900 using a user interface (e.g., the analysis device 120). By way of example, the user may define or set the one or more analyses to be performed, culture/analysis duration, media exchange time points, image acquisition time points, etc. for each chamber of the body and/or each culture device. This way, the media exchange schedule and/or image acquisition schedule can be automated specific to each chamber and thereby be individual controlled.

In some embodiments, the automated schedule for media may include a time schedule for media exchange for each chamber (and each culture device if more than one). The time schedule may include a plurality of set time points at which the valves for media injection and/or removal may be opened for a chamber for respective injection and/or removal.

In some embodiments, the settings may include a schedule for capturing images/videos of each chamber, for example, of each device 200 or 900. At set time points, the analysis device 120 may cause the image acquisition device 110 connected to the respective cover member via optical fibers to be activated and take picture/video of assigned chambers. In some embodiments, the user can indicate whether the images will be stored in the analysis system 120, used by the system 120 to control the analysis performed (e.g., using the images as feedback), among others, or any combination thereof.

This can enable fluidic and optic control of every single chamber of each device 200 and/or 900. By way of example, this can allow for designed and automated execution of many different, complex cellular assays within single culture device.

By way of examples, the settings may include intermittent flow exchange, continuous flow exchange, among others, or a combination thereof: By enabling automated continuous flow exchange, the culture device can serve as a bioreactor, enabling dynamic flow culture assays. In some embodiments, the settings may include maintaining a continuous flow through the injection-suction channels, hence, providing dynamic culture conditions at varying flow rates and regimens (constant unidirectional, reciprocating, and pulsatile flow).

In some embodiments, the step 1010 may include a step of calibrating the system 100.

Next, the method 1000 may include a step 1020 of causing fluid exchange through the channels according to the predetermined/stored settings, determined features by the analysis device 120 (e.g., when using images as feedback), among others, or any combination thereof.

In some embodiments, according to the settings, for example, the control device 600 and/or the controller 940 can cause a volume of media to be removed from a specific chamber at a specific time. For example, the control device 600 and/or the controller 940 can cause the suction pump valves specific to that chamber to open at a specific time to remove a predetermined volume of old media from the chamber and transfer it to the waste storage reservoir. The predetermined volume of old media may be based on the stored and/or programmed settings, for example, selected by the user and/or determined by the analysis device 120. In some embodiments, the timing of the valve opening may be based on the volume of old media removed. The control device 600 and/or the controller 940 can also cause a volume of media to be delivered to a specific chamber at a specific time. For example, the control device 600 and/or the controller 940 can cause the injection pump valves specific to that chamber to open at a specific time to deliver a volume of media from the corresponding media storage reservoir to a specific chamber.

In some embodiments, the method 1000 may include a step 1030 of acquiring images of one or more chambers of each device according to the schedule included in the user selected or stored settings. In some embodiments, the device 120 may store the images acquired by the image acquisition device 110. In some embodiments, the device 120 may use the acquired images to control the analysis, e.g., performed by the control device 600 and/or the cover member 910. By way of example, the acquired images may act as a feedback.

In some embodiments, if the system is using the acquired images as feedback, the method 1000 may further include a step 1040 of determining one or more features or variables using at least the acquired images. For example, the acquired images may be analyzed for next time point for media exchange, starting or continuing a cellular assay (e.g., stem cell differentiation procedure or a cell viability assay), etc.

In some embodiments, the one or more variables or features may include but are not limited to cell morphology, confluency (density), function (e.g., beating profile of cardiomyocytes) will be analyzed. The analysis device 120 may use these features to determine a flow exchange schedule (e.g., what type of media to be used at each time point, time points for exchange), among others, among others, or a combination thereof.

For example, the features and/or related settings may be generated, calculated, measured, acquired and/or obtained using the available methods, such as methods using physiology-derived features, physics-derived features, machine learning, among others, or any combination thereof.

Steps 1020-1040 may be repeated until the analysis has been finished. And if step 1040 is omitted, steps 1020 and 1030 can be repeated according to the selected settings until the analysis has finished. Also, the steps 1020, 1030 and/or 1040 do not need to be sequential and may be performed in parallel, in a different order (e.g., reverse order), etc.

After which the analysis has finished, the user may select a sterilization setting to sterilize/clean the cover member 300 and/or 910 so that that cover member can be reused.

Figure 11:
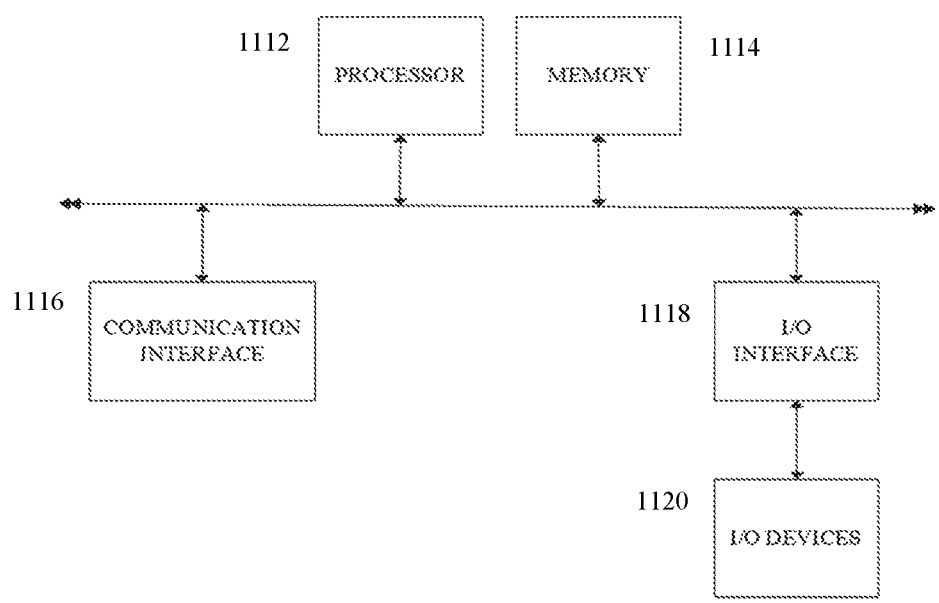
FIG. 11 shows a block diagram illustrating an example of a computing system according to embodiments.

One or more of the devices and/or systems of the system 100 may be and/or include a computer system and/or device. FIG. 11 is a block diagram showing an example of a computer system 1100. The modules of the computer system 1100 may be included in at least some of the systems and/or modules, as well as other devices and/or systems of the system 100.

The system for carrying out the embodiments of the methods disclosed herein is not limited to the systems shown in FIGS. 1 and 11. Other systems may also be used. It is also to be understood that the system 1100 may omit any of the modules illustrated and/or may include additional modules not shown.

The system 1100 shown in FIG. 11 may include any number of modules that communicate with each other through electrical or data connections (not shown). In some embodiments, the modules may be connected via any network (e.g., wired network, wireless network, or any combination thereof).

The system 1100 may be a computing system, such as a workstation, computer, or the like. The system 1100 may include one or more processors 1112. The processor(s) 1112 may include one or more processing units, which may be any known processor or a microprocessor. For example, the processor(s) may include any known central processing unit (CPU), graphical processing unit (GPU) (e.g., capable of efficient arithmetic on large matrices encountered in deep learning models), among others, or any combination thereof. The processor(s) 1112 may be coupled directly or indirectly to one or more computer-readable storage media (e.g., memory) 1114. The memory 1114 may include random access memory (RAM), read only memory (ROM), disk drive, tape drive, etc., or any combinations thereof. The memory 1114 may be configured to store programs and data, including data structures. In some embodiments, the memory 1114 may also include a frame buffer for storing data arrays.

In some embodiments, another computer system may assume the data analysis, image processing, or other functions of the processor(s) 1112. In response to commands received from an input device, the programs or data stored in the memory 1114 may be archived in long term storage or may be further processed by the processor and presented on a display.

In some embodiments, the system 1100 may include a communication interface 1116 configured to conduct receiving and transmitting of data between other modules on the system and/or network. The communication interface 1116 may be a wired and/or wireless interface, a switched circuit wireless interface, a network of data processing devices, such as LAN, WAN, the internet, or any combination thereof. The communication interface may be configured to execute various communication protocols, such as Bluetooth, wireless, and Ethernet, in order to establish and maintain communication with at least another module on the network.

In some embodiments, the system 1110 may include an input/output interface 1118 configured for receiving information from one or more input devices 1120 (e.g., a keyboard, a mouse, and the like) and/or conveying information to one or more output devices 1120 (e.g., a printer, a CD writer, a DVD writer, portable flash memory, etc.). In some embodiments, the one or more input devices 1120 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIG. 10) may be implemented using software applications that are stored in a memory and executed by the one or more processors (e.g., CPU and/or GPU) provided on the system 100. In some embodiments, the disclosed methods may be implemented using software applications that are stored in memories and executed by the one or more processors distributed across the system.

As such, any of the systems and/or modules of the system 100 may be a general purpose computer system, such as system 1100, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or any combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 8. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A culture analysis system comprising:
   a culture device including a cover configured to be secured to a main body, the main body including one or more chambers configured to hold one or more samples;
   the cover including:
   a plurality of regions configured to overlap with the chambers of the main body when the cover is secured to the main body so that each region corresponds to a chamber of the main body;
   a fluidic pathway disposed in each region and configured be in fluidic communication with a corresponding chamber, each fluidic pathway including a fluid inlet and a fluid outlet disposed in each region;
   an optical pathway disposed in each region for the corresponding chamber;
   a detection window disposed in each region for the corresponding chamber; and
   a plurality of optical fibers and one or more groups of optical ports disposed on a first side of the cover;
   each optical pathway for each region including one or more of the plurality of optical fibers that extend between the detection window and an optical port of the one or more groups of optical ports for each region.

2. The culture analysis system of claim 1, wherein the one or more of the plurality of optical fibers for each region includes one or more of optical imaging fibers and one or more of illuminating fibers.

3. The culture analysis system of claim 2, wherein the one or more groups of one or more optical ports includes at least one port for the one or more optical imaging fibers and the one or more illuminating fibers for each region.

4. The culture analysis system of claim 2, wherein the cover further includes:
one or more groups of one or more sets of fluidic connection ports disposed on a second side of the cover, the second side of the cover being different from the first side of the cover, each set of fluidic connection ports including a first connection port for the fluid inlet and a second connection port for the fluid outlet for each region.

5. The culture analysis system of claim 1, further comprising:
one or more waste storage reservoirs;
one or more media storage reservoirs; and
an electronic controller.

6. The culture analysis system of claim 5, further comprising:
a control device, the control device being in fluidic communication with the culture device.

7. The culture analysis system of claim 6, wherein the control device includes one or more groups of one or more sets of fluidic connection ports complimentary to the one or more groups of the one or more sets of fluidic connection ports of the culture device.

8. The culture analysis system of claim 7, wherein:
the control device includes one or more injection valves that is in fluidic communication with the one or more media storage reservoirs, each injection valve being in fluidic communication with a fluid inlet of the cover; and
the control device includes one or more suction valves that is in fluidic communication with the one or more waste storage reservoirs, each suction valve being in fluidic communication with a fluid outlet of the cover;
the electronic controller is configured to control each valve.

9. The culture analysis system of claim 5, wherein the cover includes the one or more waste storage reservoirs; the one or more media storage reservoirs; and the electronic controller.

10. The culture analysis system of claim 9, wherein each region of the cover includes the one or more waste storage reservoirs and the one or more media storage reservoirs.

11. The culture analysis system of claim 3, further comprising:
an image acquiring device,
the one or more groups of one or more sets of optical ports of the cover being in communication with the image acquiring device.

12. A method of performing one or more cell culture analyses, comprising:
providing (i) a culture device including a body having one or more chambers in which a sample is disposed and a cover secured to the body, (ii) one or more waste storage reservoirs, and (iii) one or more media storage reservoirs storing one or more media;
the cover including a plurality of regions that overlap with the one or more chambers of the body so that each region corresponds to a chamber of the main body, the cover including:
one or more fluidic pathways disposed in each region and in fluidic communication with a corresponding chamber, each fluidic pathway including a fluid inlet and a fluid outlet disposed in each region;
an optical pathway disposed in each region for the corresponding chamber;
a detection window disposed in each region for the corresponding chamber;
a plurality of optical fibers and one or more groups of optical ports disposed on a side of the cover; and
each optical pathway for each region including one or more of the plurality of optical fibers that extend between the detection window and an optical port of the one or more groups of optical ports for each region; and
causing fluid exchange in the one or more chambers by controlling the fluid flow rate and timing (i) between the inlet of each region corresponding to the one or more chambers and the one or more media storage reservoirs and (ii) between the outlet of each region corresponding to the one or more chambers and the one or more waste storage reservoirs, based on one or more settings.

13. The method of claim 12, wherein the fluid exchange is individually controlled for each chamber.

14. The method of claim 13, wherein the fluid exchange is automatically controlled based on one or more stored settings.

15. The method of claim 12, the method further comprising:
acquiring one or more static or dynamic images of the one or more chambers.

16. The method of claim 15, further comprising:
determining one or more features using the acquired images of the one or more chambers; and
controlling the fluid exchange for the one or more chambers based on the one or more features.

17. The method of claim 12, wherein the cover includes and/or is in fluidic communication with the one or more waste storage reservoirs and the one or more media storage reservoirs.

18. The method of claim 17, wherein each region includes and/or is in fluidic communication with the one or more waste storage reservoirs and the one or more media storage reservoirs.

19. The method of claim 18, wherein the cover includes an electronic controller and the electronic controller of the cover causes the fluid exchange in the one or more chambers.

20. The method of claim 19, wherein:
the providing includes connecting the culture device to a control device, the control device includes the one or more waste storage reservoirs, the one or more media storage reservoirs, and the electronic controller; and
the electronic controller of the control device causes the fluid exchange.

* * * * *